US007678388B2

(12) United States Patent
Mason

(10) Patent No.: US 7,678,388 B2
(45) Date of Patent: Mar. 16, 2010

(54) METHOD OF TREATING WITH CHLORINE DIOXIDE

(76) Inventor: John Y. Mason, 2642 Marco Ave., Odessa, TX (US) 79762

(*) Notice: Subject to any disclaimer, the term of this patent is extended or adjusted under 35 U.S.C. 154(b) by 748 days.

(21) Appl. No.: 11/131,021

(22) Filed: May 16, 2005

(65) Prior Publication Data

US 2006/0068029 A1    Mar. 30, 2006

Related U.S. Application Data

(60) Provisional application No. 60/572,205, filed on May 17, 2004.

(51) Int. Cl.
*A61K 33/14* (2006.01)
*C02B 11/02* (2006.01)
*A01N 59/08* (2006.01)
*A62B 7/00* (2006.01)

(52) U.S. Cl. ............... 424/661; 422/120; 422/122; 423/477

(58) Field of Classification Search .............. None
See application file for complete search history.

(56) References Cited

U.S. PATENT DOCUMENTS

| | | | |
|---|---|---|---|
| 3,585,147 A | 6/1971 | Gordon | |
| 3,920,801 A | 11/1975 | Grotheer | |
| 4,081,520 A | 3/1978 | Swindells et al. | |
| 4,084,747 A | 4/1978 | Alliger | |
| 4,250,144 A | 2/1981 | Ratigan | |
| 4,272,019 A | 6/1981 | Halaby, Jr. | |
| 4,313,827 A | 2/1982 | Ratigan et al. | |
| 4,504,442 A | 3/1985 | Rosenblatt et al. | |
| 4,590,057 A | 5/1986 | Hicks | |
| 4,681,739 A | 7/1987 | Rosenblatt et al. | |
| 4,689,169 A | 8/1987 | Mason et al. | |
| 4,731,193 A | 3/1988 | Mason et al. | |
| 4,780,333 A | 10/1988 | Smith et al. | |
| 4,823,826 A | 4/1989 | Sacco | |
| 4,889,654 A | 12/1989 | Mason et al. | |
| 4,908,188 A | 3/1990 | Jefferis, III et al. | |
| 5,141,722 A | 8/1992 | Nagashima | |
| 5,204,081 A | 4/1993 | Mason et al. | |
| 5,207,532 A | 5/1993 | Mason et al. | |
| 5,227,306 A | 7/1993 | Eltomi et al. | |
| 5,256,310 A | 10/1993 | Brooks | |
| 5,258,171 A | 11/1993 | Eltomi | |
| 5,565,180 A | 10/1996 | Spink | |
| 5,631,300 A | 5/1997 | Wellinghoff | |
| 5,707,546 A | 1/1998 | Pitochelli | |
| 5,713,137 A | 2/1998 | Fujita | |
| 5,820,822 A | 10/1998 | Kross | |
| 5,932,085 A | 8/1999 | Cowley et al. | |
| 5,968,454 A | 10/1999 | Deacon et al. | |
| 6,042,802 A | 3/2000 | Drake | |
| 6,077,495 A | 6/2000 | Speronello et al. | |
| 6,083,457 A | 7/2000 | Parkinson et al. | |
| 6,322,768 B1 | 11/2001 | Graff et al. | |
| 6,327,812 B1 | 12/2001 | Hedman et al. | |
| 6,363,734 B1 | 4/2002 | Aoyagi | |
| 6,468,479 B1 | 10/2002 | Mason et al. | |
| 6,500,465 B1 | 12/2002 | Ronlan | |
| 6,537,821 B1 | 3/2003 | Rosenblatt et al. | |
| 6,645,457 B2 * | 11/2003 | Mason et al. | ............... 423/477 |
| 2001/0036421 A1 | 11/2001 | Speronello et al. | |
| 2001/0038805 A1 | 11/2001 | Hamilton et al. | |
| 2002/0021990 A1 | 2/2002 | Cowley et al. | |
| 2002/0036284 A1 | 3/2002 | Speronello et al. | |
| 2002/0125196 A1 | 9/2002 | Rosenblatt et al. | |
| 2003/0082073 A1 | 5/2003 | Mankovitz | |
| 2003/0138371 A1 | 7/2003 | McWhorter et al. | |
| 2004/0259188 A1 | 12/2004 | Rosenblatt et al. | |
| 2005/0019210 A1 | 1/2005 | Rosenblatt et al. | |
| 2005/0031487 A1 | 2/2005 | Rosenblatt et al. | |

FOREIGN PATENT DOCUMENTS

| | | |
|---|---|---|
| DE | 3718272 | 12/1988 |
| JP | 10182106 | 7/1998 |
| WO | WO 98/50310 | 11/1998 |
| WO | WO 01/60750 A2 | 8/2001 |
| WO | WO 01/94256 A2 | 12/2001 |
| WO | WO 02/14216 | 2/2002 |

(Continued)

OTHER PUBLICATIONS

Baker, J., et al., Testimony Before Committee on Science of U.S. House of Representatives Hearing on "The Decontamination of Anthrax and Other Biological Agents," Nov. 8, 2001.
Chin, J., "Anthrax," Control of Communicable Diseases, 17$^{th}$ Ed.; 20-25 (2000) American Public Health Association (www.anthrax.osd.mil).
Coates, D., "An evaluation of the use of chlorine dioxide (Tristel One-Shot) in an automated washer/disinfector (Medivator) fitted with a chlorine dioxide generator for decontamination of flexible endoscopes," J Hosp Infect; May 48(1):55-65 (2001).
Cross, G.L.C. and Lach, V.H., "The Effects of Controlled Exposure to Formaldehyde Vapour on Spores of *Bacillus*; Globigii NCTC 10073," J. of Applied Bacteriology, 68: 461-469 (1990).
Dixon, T.C., et al., "Anthrax," The New England Journal of Medicine; 341(11):815-826 (1999).
Hawley, R.J. and Eitzen, E.M., Jr. 2001, "Protection Against Biological Warfare Agents," p. 1161-1167. In D.D. Block (ed.), Disinfection, Sterilization and Preservation; 5$^{th}$ Edition; Lippincott, Williams, and Wilkins, Philadelphia, PA.

(Continued)

*Primary Examiner*—Ernst V Arnold
(74) *Attorney, Agent, or Firm*—Heslin Rothenberg Farley & Mesiti P.C.

(57) ABSTRACT

An aqueous chlorine dioxide solution which comprises dissolved chlorine dioxide in a concentration of about 10 to 3000 mg/l, pH in the range of about 1 to 6, and a chlorine scavenging means such as sodium chlorite in a ratio in the range of about 1:4 to 1:15 (w/w) sodium chlorite to chlorine dioxide. The chlorine dioxide solution may be stored for use over a period of several days to several months.

24 Claims, No Drawings

FOREIGN PATENT DOCUMENTS

| WO | WO 02/072484 A1 | 9/2002 |
| WO | WO 03/059401 A2 | 7/2003 |
| WO | WO 03/062144 A1 | 7/2003 |
| WO | WO 03/077956 A2 | 9/2003 |
| WO | WO 03/082353 A2 | 10/2003 |
| WO | WO 2005/123145 A2 | 12/2005 |

OTHER PUBLICATIONS

Hawley, R.J. and Eitzen, E.M., Jr. (2001) Biological Weapons—A Primer for Microbiologists, Ann Rev. Microbiol. 55: 235-253.

Hawley, R.J. and Eitzen, E.M., Jr. (2000) Bioterrorism and Biological Safety, Chap. 37 in Biological Safety: Principles Practices, $3^{rd}$ ed. (ed. Fleming, D.O. and Hunt, D.L.) pp. 567-578. ASM Press.

Horinko, M.L., Office of Solid Waste and Emergency Response. Memorandum FIFRA Crisis Exemption for Anthrax Incidents [online] Nov. 30, 2001. [retrieved Apr. 27, 2004]. Retrieved from the Internet <URL: http://www.epatechbit.org/pdf/AnthraxCrisisExempt3rd.pdf>.

Ishizaki, K., et al., "Inactivation of *Bacillus* Spores by Gaseous Ozone," J. of Applied Bacteriology, 60:67-72 (1986).

Jeng D.K., et al., "Chlorine Dioxide Gas Sterilization of Oxygenators in an Industrial Scale Sterilizer: A Successful Model," Artif Organs; Oct.: 14(5):361-8(1990).

Jeng D.K., et al., "Chlorine Dioxide Gas Sterilization Under Square—Wave Conditions," Applied and Environmental Microbiology: 56(2):514-19 (1990).

Joslyn, L.J. (2001) Gaseous Chemical Sterilization, Chap. 16 of Disinfection, Sterilization and Preservation, 5th ed. (ed. S.S. Block), pp. 337-359. Lippincott, Williams & Wilkins, New York, NY.

Knapp, J.E. and Battisti, D.L., (2001) Chlorine Dioxide, Chap. 11 of Disinfection, Sterilization and Preservation, 5th ed. (ed. S.S. Block), pp. 215-227. Lippincott, Williams & Wilkins, New York, NY.

Merck Index, 12th Ed.; p. 362 "Chlorine Dioxide" (2001).

Meselson, M., et al., "The Sverdlovsk Anthrax Outbreak of 1979," Science; (266): 1202-1208 (1994).

"Removing Teak Oil Stains, Gas-out Mildew," DIY Boat Owner, 2001-#2, p. 48.

Rutala, W.A. (1996) APIC Guideline for Selection and Use of Disinfectants, Amer. J. Infection Control, 24(4): 313-342.

Vogt, B.M., et al., "How Clean is Safe? Improving the Effectiveness of Decontamination of Structures and People Following Chemical and Biological Incidents" Final Report Prepared for the U.S. Department of Energy Chemical and Biological National Security Program, ORNL/TM-2002/178, published, Oct. 2002.

Weaver-Meyers, P.L. et al., "Controlling Mold on Library Materials with Chlorine Dioxide: An Eight Year Case Study," Journal of Academic Librarianship, 455-458 (Nov. 1998).

Weaver-Meyers, P.L. et al., "Controlling Mold on Library Materials with Chlorine Dioxide: An Eight Year Case Study," Abbey Newsletter 24(4): 1-7 (Dec. 2000).

Whitney, E.A., et al., "Inactivation of *Bacillus anthracis* Spores," Emerging Infectious Diseases vol. 9, No. 6, pp. 623-627, (Jun. 2003).

Bulletin #055, "Solutions to Air Pollution Control. Corrosion Resistant Air Emissions Equipment," Plasticair, Inc., Mississauga, Ontario, Canada, Mar. 1997.

CDG Technology website, www.cdgtechnology.com; Oct. 21, 2003, hardcopy.

Fair, J.R., et al., Gas Absorption and Gas-Liquid System Design, pp. 14-1 to 14-98, at 14-4, 14-6 in Green D., ed., Perry's Chemical Engineer's Handbook, $7^{th}$ Ed., McGraw-Hill, New York, 1997.

Gildow, J.S. (2001) Anthrax: General Overview and Environmental Decontamination Recommendations, Caltech Industries, Inc., www.caltechind.com, visited Apr. 2, 2002.

Merriam-Webster's Dictionary of Law, 1996.

McWhorter, C. (2001) Chlorine Dioxide for Gas Phase Decontamination, with source code printout, creation date Nov. 30, 2001, www.cdgtechnology.com/decontamination.html.

Simpson, G.D., et al. "A Focus on Chlorine Dioxide, An Ideal Biocide," (Feb. 5, 2000), http://www.clo2.com:80/reading/waste/corrosion.html, visited Apr. 3, 2002.

* cited by examiner

METHOD OF TREATING WITH CHLORINE DIOXIDE

CROSS-REFERENCE TO RELATED APPLICATIONS

This application claims benefit of U.S. Provisional Patent Application No. 60/572,205, filed May 17, 2004.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

This invention relates to long-lasting stable aqueous chlorine dioxide solutions, as well as methods of making and using said solutions. Aqueous chlorine dioxide solutions that are long-lasting and stable are particularly useful in applications requiring relatively small amounts of chlorine dioxide treatment or intermittent treatments. Chlorine dioxide is a strong oxidizing agent finding application in a wide range of fields including bleaching, pesticides, biocides, pollution abatement, disinfectant, oil field uses, and the like.

Chlorine dioxide is commercially employed as a bleaching, fumigating, sanitizing, or sterilizing agent. Chlorine dioxide can be used to replace chlorine and hypochlorite products more particularly used in such applications with resultant benefits. Chlorine dioxide is a more powerful sterilizing agent and requires lower dose levels than chlorine. Chlorine dioxide produces lower levels of chlorinated organic compounds than chlorine when it is used to sterilize raw water containing organic compounds. Additionally, chlorine dioxide is less corrosive than chlorine to metals.

However, chlorine dioxide is an unstable, highly reactive gas which is soluble in and decomposes in water. See, e.g., U.S. Pat. No. 4,941,917. Therefore, it has heretofore been necessary to generate aqueous chlorine dioxide solutions on site for immediate use or use within a relatively short time (typically less than an hour). Due to its poor stability, it has been the practice in the industry to store chlorine dioxide in the absence of light and at reduced temperatures. This requirement of on site generation of chlorine dioxide has severely limited its utility in facilities requiring relatively small amounts of chlorine dioxide or those which have only intermittent needs.

There are a number of known methods for producing chlorine dioxide. For large chlorine dioxide requirements, it is typical to employ a chlorine dioxide generator. See for example U.S. Pat. Nos. 4,247,531, 4,590,057, and 5,204,081.

The "hypochlorous acid process," commonly achieved through depression of pH on chlorine dioxide generators, which includes many commercially available chlorite based chlorine dioxide systems, are actually not chlorine gas sodium chlorite reactions. These systems depend on the reaction of chlorine dissolved in water in the form of hypochlorus acid with sodium chlorite to form chlorine dioxide. This reaction is described in Equation 1:

$$HOCl+HCl+2ClO_2^- \rightarrow 2ClO_2+H_2O+2Cl^-$$ Equation 1

For hypochlorite ion to be predominantly in the form of hypochlorus acid the pH of the reactant solution must be below 2.8. Otherwise the dissolved chlorine will be in the form of hypochlorite ion. If this is the case the predominant reaction that occurs is shown by Equation 2:

$$OCl^-+ClO_2^- \rightarrow ClO_3^-+Cl^-$$ Equation 2

Thus at pH values above 2.8, the predominant end product of these type chlorine dioxide generators is chlorate and not chlorine dioxide.

The pH can be too low for these types of chlorine dioxide generators. At pH values below 2.3 another side reaction starts to take place as described in Equation 3:

$$ClO_2^-+4H+3Cl^- \rightarrow 2Cl_2+2H_2O$$ Equation 3

If pH is driven too low in these systems chlorite can decompose to chlorine. Therefore in hypochlorus acid type systems the operating pH range should be maintained between 2.3 and 2.8. Under laboratory conditions it has been found that in this pH, and at a concentration of 1500 mg/l of reactant chlorite, 92% of the chlorite will be converted to chlorine dioxide (Equation 1), 4% will be converted to chlorate (Equation 2), and 4% will be converted to chlorine (Equation 3). As these reactions all proceed at about the same rate, the actual pH governs the actual percentages formed.

In some applications it is particularly desirable to have chlorine free solutions of chlorine dioxide. This can be achieved with the above solutions by complex purification steps involving stripping the chlorine from solution and re-absorption of chlorine dioxide from a generating solution to a receiving solution. A stream of air is typically used for this purpose. But, this is hazardous if the concentration of chlorine dioxide in the air stream becomes high enough to initiate spontaneous decomposition. See, U.S. Pat. No. 6,274,009. Concentrations of chlorine dioxide in air above 11% can be mildly explosive.

Chlorine gas reacts rapidly with solid or aqueous sodium chlorite. In one type of chlorine dioxide generator, precursor chemicals are pre-reacted, under vacuum, in the absence of dilution water. See, U.S. Pat. No. 6,645,457. The reaction scheme for this chlorine gas sodium chlorite reaction is as follows:

$$2NaClO_2+Cl_2 \rightarrow 2ClO_2+2NaCl$$ Equation 4.

It is an advantage in this type of system that it does not dissolve chlorine gas in the dilution water. Rather, the chlorine gas is pre-reacted to form chlorine dioxide gas which is then dissolved in the dilution water.

In addition to high capital costs, these systems also require an experienced chemical operator. So, this type of system is not practical for users who require only small quantities of chlorine dioxide or require it only intermittently. Additionally, for many small or intermittent treatments, the functionality of small generation systems may not be reliable. The small application cannot justify the technical support and monitoring required to ensure the quality control parameters necessary in such operations.

As an alternative to the above generator technologies, some small scale chlorine dioxide users have turned to the so called "stabilized chlorine dioxide" products. These products are aqueous solutions of sodium chlorite that are activated at the site of use with a weak acid to produce chlorine dioxide in solution. Examples of stabilized chlorine dioxide products are found in U.S. Pat. Nos. 4,964,466, 4,941,917, and 5,031,700. A significant disadvantage of stabilized chlorine dioxide is that the weak acid activation of the chlorite is highly inefficient, producing typically less than 20% yield stabilized chlorine dioxide.

Summarizing the state of chlorine dioxide treatments, there is currently no efficient method for many industrial applications requiring relatively small amounts of chlorine dioxide.

BRIEF SUMMARY OF THE INVENTION

The purpose of the present invention is to adapt a chlorine generation system to treat a facility requiring relatively small amount of treatment or only intermittent treatment. The method comprises the steps of
  a) generating an aqueous solution of chlorine dioxide by reacting sodium chlorite with chlorine to form chlorine dioxide and dissolving the chlorine dioxide in water;
  b) collecting and storing the aqueous solution of chlorine dioxide in an appropriate container at the site of use, the amount of aqueous chlorine dioxide stored in the container sufficient to provide from about 2 to about 100 days of treatment at the facility, and
  c) over a time period of about 2 to 100 days, dispersing the aqueous chlorine dioxide from the storage container to treat the facility.

In a preferred embodiment, the method will include an additional step:
  d) after a period of time between about 2 and 100 days, repeating steps a) and b) to recharge the container with aqueous chlorine dioxide.

The time periods recited in steps b), c), and d) are preferably about 5 to 45 days.

This cyclic process of short generation times (in the order of hours) and long dispensing and treatment times (about 2 to 100 days) results in a very efficient and cost effective operation. This process lends itself to the use of portable generators that can service a number of sites equipped with the storage containers.

Preferably, the aqueous chlorine dioxide generated and stored at each site will have the following properties:
  chlorine dioxide concentration: 10 to 3000 mg/liter of water, preferably from 1000 to 2500 mg/l;
  pH from 1 to 6.5; preferably from 3 to 6.0; and
  attendant chlorite concentration: from 1 to 3000 mg/l of chlorite ions, preferably from 100 to 1000 mg/l;
  Ratio of chlorite to chlorine dioxide from 1:1 to 1:15, preferably 1:4 to 1:13, more preferably 1:4 to 1:10.

BRIEF DESCRIPTION OF THE SEVERAL VIEWS OF THE DRAWING

Not Applicable.

DETAILED DESCRIPTION OF THE INVENTION

As mentioned above, the method of the present invention is particularly adapted to treat certain facilities with relatively small amounts of aqueous chlorine dioxide. These facilities include, but are not limited to, pulp bleaching, disinfectant or biocide in municipal and industrial water systems, cooling towers, swimming pools, small food and beverage facilities, greenhouse water systems, animal husbandry operations, oil field pollution abatement, oil field treatments, fumigation, medical laboratories and facilities, and the like. The treatment sequence for small operations includes a very short period of generating followed by a long period of storing aqueous chlorine dioxide treating the facility with aqueous chlorine dioxide that can be continuous or intermittent.

In its broadest embodiment, the method for treating a particular facility comprises the following distinct steps: generation of aqueous chlorine dioxide, quality control, storage of the generated chlorine dioxide, and dispensing of the aqueous chlorine dioxide for the treatment of the facility. The equipment for carrying out these steps may be as follows:

Generation of aqueous chlorine dioxide: The chlorine dioxide usable in the present invention is referred to herein as chlorite/chlorine generated chlorine dioxide, to distinguish it from stabilized chlorine dioxide described above. The chlorite/chlorine chlorine dioxide is generated by reacting a chlorite such as sodium chlorite with chlorine. The reaction produces chlorine dioxide gas which is immediately dissolved in a water stream to form an aqueous solution of chlorine dioxide (referred to as aqueous chlorine dioxide). There are several commercial generators for producing the chlorite/chlorine chlorine dioxide. Suitable generators are disclosed in U.S. Pat. Nos. 4,247,531; 5,204,081; 6,468,479; and 6,645,457, the disclosures of which are incorporated herein by reference.

Storage: Although almost any type of pressure tight tank or container may be used, it is preferred to employ a tank with an internal bladder that expands on the charging of the tank and contracts upon the discharge of the aqueous chlorine dioxide.

Use of a bladder eliminates the need for head space and an exit fume scrubber. The tank or container should be large enough to contain the required amount of chlorine dioxide solution (e.g. 5 to 100 days of treatment). Tanks having a capacity of from 5 gallons to 10,000 gallons should be satisfactory for most operations. The pressure maintained in the tank will be relatively low, in the order of 0 psi to 20 psi. It has been discovered that the tank need not be stored in a light free environment or at low temperatures. The examples described below reveal that the chlorine dioxide solution may be stored in the tank at temperatures ranging from a low at night of 78 degrees F. to a high of 105 degrees F. during the day.

Dispensing of chlorine dioxide solution: Once the tank is charged, the generator is disconnected freeing it to move to another location. The tank may then be connected to the treatment equipment for the facility (e.g. hoses or pipes in a distribution system provided with nozzles or sprays). A pump is generally required to pump the treating solution from the tank through the distribution system.

Operation. The best mode for carrying out the method of the present invention, as presently contemplated, involves the location of the chlorine dioxide solution containers (e.g. tanks) at a number of plants that can be serviced by a portable generator unit. The plants are the facilities to be treated with chlorine dioxide and may be large plants such as an industrial water system or a small plant such as a swimming pool or a greenhouse.

The generator unit is mounted on a truck or trailer and transported to the site to be treated. The unit, of course, will include instrumentation, controls and piping necessary to generate chlorine dioxide of proper specs for the intended treatment. A preferred generator is commercially available from Sabre Oxidation Technologies, Inc. of Odessa Tex. This generator is described in U.S. Pat. No. 6,468,479.

At the plant site, the generator unit with the precursor chemicals is connected to a suitable water source. The generator discharges a stream of an aqueous solution of chlorine dioxide, which is piped to the storage tank. With the tank charged to the desired level, the generator unit is disconnected, placing the tank ready for treating the plant. The dispensing of the treating solution is under the control of the plant operator who may be guided by a treating schedule developed in accordance with industry practices.

The generator unit may be moved from site to site charging the storage containers at each site in accordance with its prescribed specifications and schedule.

The operator of the generator is a skilled technician insuring that the treating solution meets the specifications of the plant treatment. The plant operator is provided with a delivery sheet verifying the chlorine dioxide content of the product via an acceptable standard method such as AWWA 4500-Cl02-E, or equivalent.

A significant operational advantage of the present invention over the conventional method of site generation and application of chlorine dioxide is the efficient use of generators and support personnel. As mentioned previously, the generation phase of the present invention is only a fraction of the treating phase of the cycle. The generator and support personnel are at the use site for only a few hours, whereas the treatment may continue for days or weeks using plant personnel and relatively simple dispensing and distribution procedures.

Thus, in a first embodiment, the invention provides an aqueous solution of chlorine dioxide that is stable over a long storage period, comprising:
 a) dissolved chlorine dioxide, and
 b) chlorine scavenging means (e.g. sodium chlorite) for converting dissolved chlorine to chlorine dioxide, said aqueous solution being prepared to initially have a chlorine dioxide concentration preferably in the range of about 2000 to 3000 mg/l, most preferably about 2280 mg/l, pH preferably in the range of 5 to 6, most preferably about 5, and a ratio of chlorine scavenging means:chlorine dioxide preferably in the range of 1:4 to 1:15, more preferably 1:4 to 1:10 (w/w) based on a sodium chlorite to chlorine dioxide system,
  wherein the pH and ratio of the initially prepared aqueous solution are selected so that the chlorine dioxide concentration in the aqueous solution may be maintained at normal atmospheric pressure over a storage period of at least 45 days, preferably at least 90 days with less than 10% loss in concentration, and preferably less than 5% loss in concentration of the chlorine dioxide.

In a second embodiment, the invention provides a method for making an aqueous solution of chlorine dioxide that is stable over a long storage period, comprising:
 a) dissolving chlorine dioxide in water, and
 b) adding a chlorine scavenging means for converting dissolved chlorine to chlorine dioxide,
  wherein said aqueous solution is prepared to initially have a chlorine dioxide concentration preferably in the range of about 2000 to 3000 mg/l, more preferably about 2280 mg/l, pH preferably in the range of 5 to 6, most preferably about 5.1, and a ratio of chlorine scavenging means:chlorine dioxide preferably in the range of 1:4 to 1:15, more preferably 1:4 to 1:10 (w/w) based on a sodium chlorite to chlorine dioxide system,
  wherein the pH and ratio of the initially prepared aqueous solution are selected so that the chlorine dioxide concentration in the aqueous solution may be maintained at normal atmospheric pressure over a storage period of at least 45 days, preferably at least 90 days with less than 10% loss in concentration, and preferably less than 5% loss in concentration of the chlorine dioxide.

In a third embodiment, the invention provides a method for distributing aqueous chlorine dioxide that is stable over a long storage period comprising the steps of
 a) making an aqueous solution of chlorine dioxide by dissolving chlorine dioxide in water, and adding a chlorine scavenging means for converting dissolved chlorine to chlorine dioxide,
 b) filling a storage container with the aqueous solution of chlorine dioxide for use by an end-user over said long storage period, and
 c) maintaining the chlorine dioxide concentration of the aqueous solution in said storage container,
  wherein said aqueous solution is prepared to initially have a chlorine dioxide concentration preferably in the range of about 2000 to 3000 mg/l, more preferably about 2280 mg/l, pH preferably in the range of 5 to 6, most preferably about 5.1, and a ratio of chlorine scavenging means:chlorine dioxide preferably in the range of 1:4 to 1:15, more preferably 1:4 to 1:10 (w/w) based on a sodium chlorite to chlorine dioxide system,
  wherein the pH and ratio of the initially prepared aqueous solution are selected so that the chlorine dioxide concentration in the aqueous solution may be maintained at normal atmospheric pressure over a storage period of at least 45 days, preferably at least 90 days with less than 10% loss in concentration, and preferably less than 5% loss in concentration of the chlorine dioxide.

In a fourth embodiment, the invention provides a method for using aqueous chlorine dioxide that is stable over a long storage period comprising the steps of:
 a) making an aqueous solution of chlorine dioxide by dissolving chlorine dioxide in water, and adding a chlorine scavenging means for converting dissolved chlorine to chlorine dioxide,
 b) filling a storage container with the aqueous solution of chlorine dioxide for use by an end-user over said long storage period,
 c) maintaining the chlorine dioxide concentration of the aqueous solution in said storage container, and
 d) dispensing the aqueous chlorine dioxide solution from the storage container for use as needed over a period of at least about 45 days or longer, preferably at least about 90 days or longer,
  wherein said aqueous solution is prepared to initially have a chlorine dioxide concentration preferably in the range of about 2000 to 3000 mg/l, more preferably about 2280 mg/l, pH preferably in the range of 5 to 6, most preferably about 5.1, and a ratio of chlorine scavenging means:chlorine dioxide preferably in the range of 1:4 to 1:15, more preferably 1:4 to 1:10 (w/w) based on a sodium chlorite to chlorine dioxide system,
  wherein the pH and ratio of the initially prepared aqueous solution are selected so that the chlorine dioxide concentration in the aqueous solution may be maintained at normal atmospheric pressure over a storage period of at least 45 days, preferably at least 90 days with less than 10% loss in concentration, and preferably less than 5% loss in concentration of the chlorine dioxide.

Example 1

An aqueous solution of 1600 mg/l chlorine dioxide with a pH of 5.6 and a sodium chlorite content of 110 mg/l is prepared and standardized method 4500-ClO2-E. The initial ratio of sodium chlorite to chlorine dioxide in the aqueous solution is 1:15 (w/w). The generation method is that disclosed in U.S. Pat. No. 6,468,479. The solution is stored in a standard clear polyethylene "tote" tank. The tank is filled to about ⅔ capacity and outside in the direct sunlight. The ambient temperature during the test period ranges from 78 degrees F. to 105 degrees F. During the test period, the concentration of the chlorine dioxide in the solution declines as follows:

| Elapsed time | Chlorine dioxide concentration |
| --- | --- |
| 14 days | 1480 mg/l (7.5% loss) |
| 30 days | 1442 mg/l (9.9% loss) |
| 45 days | 1433 mg/l (10.4% loss) |

Example 2

A test identical to Example 1 is carried out except the sample is 2280 mg/l of a chlorine dioxide solution having a pH of 5.1 and a sodium chlorite content of 180 mg/l. The initial ratio of sodium chlorite to chlorine dioxide in the aqueous solution is 1:13 (w/w). The test results are as follows:

| Elapsed time | Chlorine dioxide concentration |
| --- | --- |
| 14 days | 2220 mg/l (2.6% loss) |
| 30 days | 2198 mg/l (3.6% loss) |
| 45 days | 2195 mg/l (3.7% loss) |
| 90 days | 2190 mg/l (3.9% loss) |

The above tests demonstrate that chlorine dioxide solutions can safely be stored for long periods of time in direct sunlight and at relatively high temperatures without excessive decomposition. Test 2 also demonstrates that the chlorine dioxide concentration stays more constant in a solution having a slightly lower pH of about 5.1, a slightly higher ratio of sodium chlorite to chlorine dioxide of about 1:13, and a slightly higher chlorine dioxide concentration of about 2280 mg/l.

Example 3

A test is being conducted to observe and evaluate the stability and decay of chlorine dioxide ($ClO_2$) at various concentrations and pH over time. The table below represents the targeted concentrations of $ClO_2$, sodium chlorite ("chlorite or $ClO_2^-$") and target pH.

The storage containers used in this Example 3 were different from those used in Examples 1 and 2, above. In this Example 3, the storage containers have a lot of relative headspace resulting in losses every time the container is opened to take a sample. This illustrates the desirability of minimizing headspace during storage.

|  | 1500 ppm | | 2000 ppm | | 2500 ppm | |
| --- | --- | --- | --- | --- | --- | --- |
| ClO2 | pH 5 | pH 6 | pH 5 | pH 6 | pH 5 | pH 6 |
| Chlorite | 0 | 0 | 0 | 0 | 0 | 0 |
|  | 250 | 250 | 250 | 250 | 250 | 250 |
|  | 500 | 500 | 500 | 500 | 500 | 500 |

It should be noted that the solutions prepared were not "exactly" as it appears in the table but approximations due the variables involved in the preparation of the chlorine dioxide. Having said that, the data presented below shows 1) the volume used in the preparation of $ClO_2$ 2) the initial concentration and pH and 3) the concentrations obtained over time.

The analytical method by which the concentrations are being determined is titration (procedure is shown below).

The reagents used are:
a) Phosphate Buffer Solution, pH 7 (Chem. Lab. Prod. No. LC18520-4);
b) Hydrochloric Acid, 6N (HCl);
c) Potassium Iodide free flowing granular—Certified (KI) (Fisher Scientific Prod. No P410-10);
d) Sodium Thiosulfate, 0.1N—Standard Certified (Fisher Scientific Prod. No. SS368-20); and
e) Deionized water, DI The titration procedure used is:
a) Add 150 mL DI water to a 250 mL beaker;
b) Add 1 gram (approx.) of granular KI;
c) Add 5 mL of phosphate buffer pH7;
d) Mix solution in container by gently rocking the container 5 times before sample transfer;
e) Using a 5 mL pipette transfer 5 mL solution into beaker;
f) Titrate to clear, colorless endpoint with 0.1N sodium thiosulfate solution;
g) Record mLs of titrant under column A;
h) Add 5 mL of 6N HCl;
i) Titrate to clear, colorless endpoint with 0.1N sodium thiosulfate solution;
j) Record mLs of titrant under column B;
k) Measure and record pH under corresponding column; and
l) Calculate $ClO_2$ and $ClO_2^-$ concentration and log results under corresponding column;

The calculations are as follows:

$$\text{Chlorine Dioxide mg/L as } ClO_2 = \frac{A \times N \times 67{,}450}{V_{sample}}$$

$$\text{Chlorite, mg/L as } ClO_2^- = \frac{(B - 4A) \times N \times 16{,}860}{V_{sample}}$$

Where:
A=Volume (mL) of Std. sodium thiosulfate
B=Volume (mL) of Std. sodium thiosulfate after adding 5 mL of HCl
N=Normality of Sodium thiosulfate
$V_{sample}$=Volume of sample used
67,450=(Equivalent weight of Chlorine Dioxide)×1000 mg/g (as Eq. Wt.)
16,860=(Equivalent weight of Chlorite)×1000 mg/g (as Eq. Wt)

Based on the data obtained thus far the following can be observed:
a) The decay of both chlorine dioxide and chlorite is clearly observed, however the rate at which this occurs varies between pH's especially with chlorite.
b) It appears that the optimum pH range depends on the concentration of both chlorine dioxide and chlorite. In the low range both chlorine dioxide and chlorite have a more stable relationship at 1500/500 and a pH 6.
c) At the 2000 ppm range, both chlorine dioxide and chlorite are more stable at 2000/500 ppm and a pH of 5.
d) At 2500 ppm chlorine dioxide holds better at a pH of 5 while chlorite prefers to be at pH 6.

Solution #1

| Preparation: | | Target concentration: | |
|---|---|---|---|
| Acid | 2.6 | $ClO_2$ | 1500 |
| Bleach | 7.6 | $ClO_2^-$ | 0 |
| Chlorite | 5.0 | pH (approx) | 5 |
| $H_2O$ | 484.8 | | |
| mL | 500.0 | | |

| Week # | mL titated | | ppm | | pH |
| | A | B | $ClO_2$ | Chlorite | |
|---|---|---|---|---|---|
| 0 | 1.1 | 4.55 | 1484 | 51 | 5.06 |
| 1 | 1.1 | 4 | 1416 | 0 | 3.03 |
| 2 | 1.0 | 3.85 | 1282 | 17 | 2.84 |
| 3 | 0.9 | 3.6 | 1214 | 0 | 2.84 |
| 4 | 0.9 | 3.45 | 1147 | 17 | 2.82 |
| 5 | 0.9 | 3.2 | 1147 | 0 | 2.76 |

Solution #2

| Preparation: | | Target concentration: | |
|---|---|---|---|
| Acid | 2.6 | $ClO_2$ | 1500 |
| Bleach | 7.6 | $ClO_2^-$ | 250 |
| Chlorite | 7.0 | pH (approx) | 5 |
| $H_2O$ | 482.8 | | |
| mL | 500.0 | | |

| Week # | mL titated | | ppm | | pH |
| | A | B | $ClO_2$ | Chlorite | |
|---|---|---|---|---|---|
| 0 | 1.1 | 5.25 | 1416 | 354 | 4.01 |
| 1 | 0.9 | 5 | 1214 | 472 | 4.24 |
| 2 | 0.8 | 4.8 | 1079 | 540 | 4.63 |
| 3 | 0.7 | 4.55 | 944 | 590 | 4.99 |
| 4 | 0.7 | 4.3 | 944 | 506 | 4.06 |
| 5 | 0.7 | 4.05 | 944 | 422 | 5.29 |

Solution #3

| Preparation: | | Target concentration: | |
|---|---|---|---|
| Acid | 2.6 | $ClO_2$ | 1500 |
| Bleach | 7.6 | $ClO_2^-$ | 500 |
| Chlorite | 6.5 | pH (approx) | 5 |
| $H_2O$ | 483.3 | | |
| mL | 500.0 | | |

| Week # | mL titated | | ppm | | pH |
| | A | B | $ClO_2$ | Chlorite | |
|---|---|---|---|---|---|
| 0 | 1.1 | 6 | 1484 | 540 | 4.45 |
| 1 | 1.0 | 5.8 | 1349 | 607 | 5.57 |
| 2 | 1.1 | 5.4 | 1484 | 337 | 5.52 |
| 3 | 0.9 | 5.1 | 1214 | 506 | 5.42 |
| 4 | 0.9 | 4.9 | 1147 | 506 | 4.6 |
| 5 | 0.8 | 4.7 | 1079 | 506 | 5.52 |

Solution #4

| Preparation: | | Target concentration: | |
|---|---|---|---|
| Acid | 2.6 | $ClO_2$ | 1500 |
| Bleach | 7.0 | $ClO_2^-$ | 0 |
| Chlorite | 5.0 | pH (approx) | 6 |
| $H_2O$ | 485.4 | | |
| mL | 500.0 | | |

| Week # | mL titated | | ppm | | pH |
| | A | B | $ClO_2$ | Chlorite | |
|---|---|---|---|---|---|
| 0 | 1.1 | 4.7 | 1484 | 101 | 6.5 |
| 1 | 1.05 | 4.4 | 1416 | 67 | 5.76 |
| 2 | 1.0 | 4.3 | 1349 | 101 | 5.55 |
| 3 | 0.95 | 4.0 | 1282 | 67 | 5.16 |
| 4 | 0.9 | 3.5 | 1214 | 0 | 3.36 |
| 5 | 0.85 | 3.3 | 1147 | 0 | 3.05 |

Solution #5

| Preparation: | | Target concentration: | |
|---|---|---|---|
| Acid | 2.6 | $ClO_2$ | 1500 |
| Bleach | 7.6 | $ClO_2^-$ | 250 |
| Chlorite | 5.4 | pH (approx) | 6 |
| $H_2O$= | 484.4 | | |
| mL | 500.0 | | |

| Week # | mL titated | | ppm | | pH |
| | A | B | $ClO_2$ | Chlorite | |
|---|---|---|---|---|---|
| 0 | 1.2 | 5.5 | 1619 | 236 | 6.5 |
| 1 | 1.0 | 4.7 | 1349 | 236 | 5.68 |
| 2 | 1.1 | 4.5 | 1484 | 34 | 5.59 |
| 3 | 0.9 | 4.3 | 1214 | 236 | 5.46 |
| 4 | 0.9 | 4.1 | 1214 | 169 | 5.18 |
| 5 | 0.9 | 3.8 | 1147 | 135 | 5.46 |

Solution #6

| Preparation: | | Target concentration: | |
|---|---|---|---|
| Acid | 2.6 | $ClO_2$ | 1500 |
| Bleach | 7.6 | $ClO_2^-$ | 500 |
| Chlorite | 6.0 | pH (approx) | 6 |
| $H_2O$= | 483.8 | | |
| mL | 500.0 | | |

| Week # | mL titated | | ppm | | pH |
| | A | B | $ClO_2$ | Chlorite | |
|---|---|---|---|---|---|
| 0 | 1.1 | 5.6 | 1416 | 472 | 6.65 |
| 1 | 1.0 | 5.15 | 1282 | 455 | 5.81 |
| 2 | 0.9 | 4.9 | 1214 | 438 | 5.69 |
| 3 | 0.85 | 4.55 | 1147 | 388 | 5.6 |
| 4 | 0.8 | 4.2 | 1079 | 337 | 5.35 |
| 5 | 0.75 | 4.2 | 1012 | 405 | 5.65 |

Solution #7

| Preparation: | | Target concentration: | |
|---|---|---|---|
| Acid | 4.4 | $ClO_2$ | 2000 |
| Bleach | 8.4 | $ClO_2^-$ | 0 |
| Chlorite | 6.0 | pH (approx) | 5 |
| $H_2O$= | 481.2 | | |
| mL | 500.0 | | |

| Week # | mL titated | | ppm | | pH |
| | A | B | $ClO_2$ | Chlorite | |
|---|---|---|---|---|---|
| 0 | 1.6 | 5.9 | 2091 | 0 | 4.35 |
| 1 | 1.5 | 5.55 | 1956 | 0 | 2.8 |

-continued

| | | | | | |
|---|---|---|---|---|---|
| 2 | 1.3 | 5.25 | 1754 | 17 | 2.59 |
| 3 | 1.3 | 4.9 | 1754 | 0 | 2.56 |
| 4 | 1.2 | 4.5 | 1551 | 0 | 2.6 |
| 5 | 1.1 | 4.15 | 1484 | 0 | 2.51 |

Solution #8

| Preparation: | | Target concentration: | |
|---|---|---|---|
| Acid | 4.4 | $ClO_2$ | 2000 |
| Bleach | 8.4 | $ClO_2^-$ | 250 |
| Chlorite | 6.9 | pH (approx) | 5 |
| $H_2O=$ | 480.3 | | |
| mL | 500.0 | | |

| | mL titated | | ppm | | |
|---|---|---|---|---|---|
| Week # | A | B | $ClO_2$ | Chlorite | pH |
| 0 | 1.5 | 6.95 | 2024 | 320 | 4.13 |
| 1 | 1.5 | 6.5 | 1956 | 236 | 5.08 |
| 2 | 1.4 | 6.35 | 1821 | 320 | 5.42 |
| 3 | 1.3 | 5.1 | 1754 | 0 | 5.15 |
| 4 | 1.3 | 5.7 | 1754 | 169 | 5.44 |
| 5 | 1.25 | 5.25 | 1686 | 84 | 5.51 |

Solution #9

| Preparation: | | Target concentration: | |
|---|---|---|---|
| Acid | 4.4 | $ClO_2$ | 2000 |
| Bleach | 8.4 | $ClO_2^-$ | 500 |
| Chlorite | 8.9 | pH (approx) | 5 |
| $H_2O=$ | 478.3 | | |
| mL | 500.0 | | |

| | mL titated | | ppm | | |
|---|---|---|---|---|---|
| Week # | A | B | $ClO_2$ | Chlorite | pH |
| 0 | 1.5 | 8.2 | 2024 | 742 | 4.52 |
| 1 | 1.5 | 7.9 | 1956 | 708 | 5.68 |
| 2 | 1.4 | 7.6 | 1889 | 674 | 5.68 |
| 3 | 1.3 | 7.0 | 1754 | 607 | 5.28 |
| 4 | 1.3 | 6.80 | 1754 | 540 | 5.41 |
| 5 | 1.25 | 6.3 | 1686 | 438 | 5.64 |

Solution #10

| Preparation: | | Target concentration: | |
|---|---|---|---|
| Acid | 4.40 | $ClO_2$ | 2000 |
| Bleach | 8.40 | $ClO_2^-$ | 0 |
| Chlorite | 6.00 | pH (approx) | 6 |
| $H_2O$ | 481.20 | | |
| mL | 500.00 | | |

| | mL titated | | ppm | | |
|---|---|---|---|---|---|
| Week # | A | B | $ClO_2$ | Chlorite | pH |
| 0 | 1.55 | 5.9 | 2091 | 0 | 6.12 |
| 1 | 1.40 | 5.5 | 1889 | 0 | 2.76 |
| 2 | 1.35 | 5.05 | 1821 | 0 | 2.53 |
| 3 | 1.25 | 4.9 | 1686 | 0 | 2.57 |
| 4 | 1.25 | 4.4 | 1686 | 0 | 2.6 |
| 5 | 1.15 | 4.4 | 1551 | 0 | 2.36 |

Solution #11

| Preparation: | | Target concentration: | |
|---|---|---|---|
| Acid | 4.40 | $ClO_2$ | 2000 |
| Bleach | 8.40 | $ClO_2^-$ | 250 |
| Chlorite | 6.90 | pH (approx) | 6 |
| $H_2O=$ | 480.30 | | |
| mL | 500.00 | | |

| | mL titated | | ppm | | |
|---|---|---|---|---|---|
| Week # | A | B | $ClO_2$ | Chlorite | pH |
| 0 | 1.55 | 7.05 | 2091 | 287 | 6.3 |
| 1 | 1.50 | 6.8 | 2024 | 270 | 5.63 |
| 2 | 1.40 | 6.3 | 1889 | 236 | 5.54 |
| 3 | 1.30 | 5.9 | 1754 | 236 | 5.29 |
| 4 | 1.30 | 5.5 | 1754 | 101 | 5.27 |
| 5 | 1.25 | 5.35 | 1686 | 118 | 5.4 |

Solution #12

| Preparation: | | Target concentration: | |
|---|---|---|---|
| Acid | 4.40 | $ClO_2$ | 2000 |
| Bleach | 8.40 | $ClO_2^-$ | 500 |
| Chlorite | 7.80 | pH (approx) | 6 |
| $H_2O=$ | 479.40 | | |
| mL | 500.00 | | |

| | mL titated | | ppm | | |
|---|---|---|---|---|---|
| Week # | A | B | $ClO_2$ | Chlorite | pH |
| 0 | 1.55 | 7.7 | 2091 | 506 | 5.84 |
| 1 | 1.50 | 7 | 2024 | 337 | 5.58 |
| 2 | 1.40 | 6.7 | 1889 | 371 | 5.53 |
| 3 | 1.35 | 6.3 | 1821 | 303 | 5.12 |
| 4 | 1.20 | 5.9 | 1619 | 371 | 5.52 |
| 5 | 1.35 | 5.5 | 1821 | 34 | 5.52 |

Solution #13

| Preparation: | | Target concentration: | |
|---|---|---|---|
| Acid | 5.20 | $ClO_2$ | 2500 |
| Bleach | 10.00 | $ClO_2^-$ | 0 |
| Chlorite | 7.20 | pH (approx) | 5 |
| $H_2O=$ | 477.60 | | |
| mL | 500.00 | | |

| | mL titated | | ppm | | |
|---|---|---|---|---|---|
| Week # | A | B | $ClO_2$ | Chlorite | pH |
| 0 | 1.80 | 7 | 2428 | 0 | 5.08 |
| 1 | 1.65 | 6.4 | 2226 | 0 | 2.67 |
| 2 | 1.60 | 6.1 | 2158 | 0 | 2.48 |
| 3 | 1.50 | 5.6 | 2024 | 0 | 2.49 |
| 4 | 1.35 | 5.35 | 1821 | 0 | 2.55 |
| 5 | 1.30 | 5.1 | 1754 | 0 | 2.31 |

Solution #14

| Preparation: | | Target concentration: | |
|---|---|---|---|
| Acid | 5.30 | $ClO_2$ | 2500 |
| Bleach | 10.00 | $ClO_2^-$ | 250 |

-continued

| | | | | |
|---|---|---|---|---|
| Chlorite | 8.00 | pH (approx) | | 5 |
| H₂O= mL | 476.70 500.00 | | | |

| | mL titated | | ppm | | |
|---|---|---|---|---|---|
| Week # | A | B | ClO₂ | Chlorite | pH |
| 0 | 1.80 | 7.8 | 2428 | 202 | 4.45 |
| 1 | 1.80 | 7.6 | 2428 | 135 | 5.23 |
| 2 | 1.70 | 7.1 | 2293 | 101 | 5.58 |
| 3 | 1.60 | 6.1 | 2158 | 0 | 2.75 |
| 4 | 1.40 | 5.7 | 1889 | 34 | 2.63 |
| 5 | 1.55 | 4.9 | 2091 | 0 | 2.30 |

Solution #15

| Preparation: | | Target concentration: | |
|---|---|---|---|
| Acid | 5.20 | ClO₂ | 2500 |
| Bleach | 10.00 | ClO₂⁻ | 500 |
| Chlorite | 8.80 | pH (approx) | 5 |
| H₂O= mL | 476.00 500.00 | | |

| | mL titated | | ppm | | |
|---|---|---|---|---|---|
| Week # | A | B | ClO₂ | Chlorite | pH |
| 0 | 1.85 | 8.8 | 2496 | 472 | 5 |
| 1 | 1.80 | 8.2 | 2428 | 337 | 5.65 |
| 2 | 1.65 | 7.8 | 2226 | 405 | 5.61 |
| 3 | 1.55 | 7.3 | 2091 | 371 | 5.39 |
| 4 | 1.50 | 7.0 | 2024 | 337 | 5.32 |
| 5 | 1.50 | 6.4 | 2024 | 135 | 5.59 |

Solution #16

| Preparation: | | Target concentration: | |
|---|---|---|---|
| Acid | 5.00 | ClO₂ | 2500 |
| Bleach | 10.00 | ClO₂⁻ | 0 |
| Chlorite | 5.00 | pH (approx) | 6 |
| H₂O= mL | 480.00 500.00 | | |

| | mL titated | | ppm | | |
|---|---|---|---|---|---|
| Week # | A | B | ClO₂ | Chlorite | pH |
| 0 | 1.85 | 5.4 | 2496 | 0 | 6.4 |
| 1 | 1.20 | 4 | 1619 | 0 | 2.56 |
| 2 | 1.00 | 3.3 | 1349 | 0 | 2.39 |
| 3 | 0.90 | 3.1 | 1214 | 0 | 2.38 |
| 4 | 0.70 | 3.0 | 944 | 67 | 2.39 |
| 5 | 0.60 | 2.0 | 809 | 0 | 2.27 |

Solution #17

| Preparation: | | Target concentration: | |
|---|---|---|---|
| Acid | 5.20 | ClO₂ | 2500 |
| Bleach | 10.00 | ClO₂⁻ | 250 |
| Chlorite | 8.20 | pH (approx) | 6 |
| H₂O= mL | 476.60 500.00 | | |

| | mL titated | | ppm | | |
|---|---|---|---|---|---|
| Week # | A | B | ClO₂ | Chlorite | pH |
| 0 | 1.80 | 7.9 | 2428 | 236 | 5.45 |
| 1 | 1.60 | 7.4 | 2158 | 337 | 5.6 |
| 2 | 1.60 | 7 | 2158 | 202 | 5.6 |
| 3 | 1.70 | 5.8 | 2293 | 0 | 3.1 |
| 4 | 1.35 | 5.5 | 1821 | 34 | 2.76 |
| 5 | 1.30 | 4.9 | 1754 | 0 | 2.45 |

Solution #18

| Preparation: | | Target concentration: | |
|---|---|---|---|
| Acid | 5.20 | ClO₂ | 2500 |
| Bleach | 10.00 | ClO₂⁻ | 500 |
| Chlorite | 8.80 | pH (approx) | 6 |
| H₂O= mL | 476.00 500.00 | | |

| | mL titated | | ppm | | |
|---|---|---|---|---|---|
| Week # | A | B | ClO₂ | Chlorite | pH |
| 0 | 1.70 | 8.4 | 2293 | 540 | 6.53 |
| 1 | 1.60 | 7.85 | 2158 | 489 | 5.03 |
| 2 | 1.40 | 7.3 | 1889 | 573 | 5.67 |
| 3 | 1.35 | 6.8 | 1821 | 472 | 5.25 |
| 4 | 1.30 | 6.4 | 1754 | 405 | 5.31 |
| 5 | 1.30 | 6.0 | 1754 | 270 | 5.57 |

In summary, it is apparent from the foregoing description, the present invention provides an efficient, cost effective method for the chlorine dioxide treatment of many facilities, particularly those requiring small-scale treatments. The advantages over on site treatment with generators has been described previously. In comparison with stabilized chlorine dioxide, the present invention offers greater advantages: 1) the plant operator does not have to mix the end use product which inherently involves human error and requires some skill to reproduce quality control; 2) reduces personnel potential for exposure to concentrated precursor chemicals and eliminates on site storage of corrosive precursors; 3) the chlorite/chlorine generation is far more efficient than the stabilized chlorine dioxide (90 to 95% vs less than 20% conversion of chlorite to chlorine dioxide); 4) the pH control of the stored chlorine dioxide solution is more assured using the generator than the stabilized product, insuring the proper pH for the treatment and minimizing corrosion; 5) the chlorine dioxide concentration in the stored tank in accordance with the present invention is known and fixed; whereas in the weak acid activation system, side reactions inherent in such systems result in a continuously changing and unpredictable chlorine dioxide concentration.

I claim:

1. An aqueous solution of chlorine dioxide that remains stable for two or more days, comprising:
   a) dissolved chlorine dioxide, and
   b) chlorine scavenging means for converting dissolved chlorine to chlorine dioxide, said aqueous solution being prepared to initially have:
   i) a chlorine dioxide concentration in the range of about 1000 to 3000 mg/l,
   ii) a pH in the range of 1 to 6, and
   iii) a ratio of chlorine scavenging means:chlorine dioxide in the range of about 1:4 to 1:15 (w/w) based on a sodium chlorite to chlorine dioxide system.

2. The aqueous solution of chorine dioxide of claim 1, wherein the chlorine scavenging means comprises sodium chlorite.

3. The aqueous solution of chlorine dioxide of claim 1, wherein the initial chlorine dioxide concentration is in the range of about 2000 to about 3000 mg/l.

4. The aqueous solution of chorine dioxide of claim 1, wherein the initial pH is in the range of about 5 to 6.

5. The aqueous solution of chorine dioxide of claim 1, wherein the initial ratio of chlorine scavenging means:chlorine dioxide is in the range of about 1:10 to 1:15.

6. The aqueous solution of chorine dioxide of claim 1, wherein the initial chlorine dioxide concentration is in the range of about 2000 to 3000 mg/l, the initial pH is in the range of about 5 to 6, the chlorine scavenging means comprises sodium chlorite, and the initial ratio of sodium chlorite to chlorine dioxide is in the range of about 1:10 to 1:15.

7. The aqueous solution of chlorine dioxide of claim 1, wherein the initial concentration of chlorine dioxide decomposes by less than 10% over two or more days.

8. The aqueous solution of chlorine dioxide of claim 1, wherein said solution remains stable for 30 days or more.

9. The aqueous solution of chlorine dioxide of claim 1, wherein said solution remains stable for 45 days or more.

10. The aqueous solution of chlorine dioxide of claim 1, wherein said solution remains stable for 60 days or more.

11. The aqueous solution of chlorine dioxide of claim 1, wherein said solution remains stable for 90 days or more.

12. An aqueous solution of chlorine dioxide comprising:
a) dissolved chlorine dioxide, and
b) chlorine scavenging means for convening dissolved chlorine to chlorine dioxide, said aqueous solution being prepared to initially have:
i) a chlorine dioxide concentration in the range of about 2000 to 3000 mg/l,
ii) a pH in the range of about 5 to 6, and
iii) a ratio of chlorine scavenging means:chlorine dioxide in the range of about 1:10 to 1:15 (w/w), and wherein the pH and ratio of the initially prepared aqueous solution are selected so that the chlorine dioxide concentration in the aqueous solution may be maintained at normal atmospheric pressure over a storage period in the range of at least 2 to 90 days with less than 10% loss in concentration of the chlorine dioxide.

13. An aqueous solution of chlorine dioxide according to claim 12 wherein the pH is preferably about 5 and the ratio of chlorine scavenging means:chlorine dioxide is about 1:13 (w/w), wherein the aqueous solution may be maintained at normal atmospheric pressure over a storage period in the range of at least 90 days with less than 5% loss in concentration of the chlorine dioxide.

14. A method for making the aqueous solution of chlorine dioxide of claim 1, comprising:
a) dissolving chlorine dioxide in water, and
b) adding a chlorine scavenging means for converting dissolved chlorine to chlorine dioxide, thereby maintaining the chlorine dioxide concentration of the aqueous solution.

15. The method for making an aqueous solution of chlorine dioxide of claim 14, wherein the initial chlorine dioxide concentration is in the range of about 2000 to 3000 mg/l.

16. The method for making an aqueous solution of chlorine dioxide of claim 14, wherein the initial pH is in the range of about 5 to 6.

17. The method for making an aqueous solution of chlorine dioxide of claim 14, wherein the initial ratio of chlorine scavenging means:chlorine dioxide is in the range of about 1:10 to 1:15.

18. The method for making an aqueous solution of chlorine dioxide of claim 14, wherein the initial chlorine dioxide concentration is in the range of about 2000 to 3000 mg/l, the initial pH is in the range of about 5 to 6, the chlorine scavenging means comprises sodium chlorite, and the initial ratio of sodium chlorite to chlorine dioxide is in the range of about 1:10 to 1:15.

19. A method for using an aqueous solution of chlorine, dioxide that remains stable for two or more days comprising the steps of:
a) making an aqueous solution of chlorine dioxide according to claim 14,
b) filling a storage container with the aqueous solution of chlorine dioxide for use by an end-user over a period of two or more days, and
c) dispensing the aqueous chlorine dioxide solution from the storage container for use as needed over a period of at least two days.

20. The method for using the aqueous solution of chlorine dioxide of claim 19, wherein the chlorine scavenging means comprises sodium chlorite.

21. The method for using the aqueous solution of chlorine dioxide of claim 19, wherein the initial chlorine dioxide concentration is in the range of about 2000 to 3000 mg/l.

22. The method for using the aqueous solution of chlorine dioxide of claim 19, wherein the initial pH is in the range of about 5 to 6.

23. The method for using the aqueous solution of chlorine dioxide of claim 19, wherein the initial ratio of chlorine scavenging means:chlorine dioxide is in the range of about 1:10 to 1:15.

24. The method for using the aqueous solution of chlorine dioxide of claim 19, wherein the initial chlorine dioxide concentration is in the range of about 2000 to 3000 mg/l, the initial pH is in the range of about 5 to 6, the chlorine scavenging means comprises sodium chlorite, and the initial ratio of sodium chlorite to chlorine dioxide is in the range of about 1:10 to 1:15.

* * * * *